(12) United States Patent
Kitchen et al.

(10) Patent No.: US 7,324,928 B2
(45) Date of Patent: Jan. 29, 2008

(54) METHOD AND SYSTEM FOR DETERMINING PHENOTYPE FROM GENOTYPE

(76) Inventors: Scott G. Kitchen, 1420 Camden Ave. #3, Los Angeles, CA (US) 90025; Christina M. Kitchen, 1420 Camden Ave. #3, Los Angeles, CA (US) 90025

( * ) Notice: Subject to any disclaimer, the term of this patent is extended or adjusted under 35 U.S.C. 154(b) by 401 days.

(21) Appl. No.: 10/378,866

(22) Filed: Mar. 5, 2003

(65) Prior Publication Data

US 2003/0220777 A1 Nov. 27, 2003

Related U.S. Application Data

(60) Provisional application No. 60/361,703, filed on Mar. 6, 2002.

(51) Int. Cl.
*G06G 7/58* (2006.01)
*G06G 7/60* (2006.01)
(52) U.S. Cl. ............................................. 703/3; 703/11
(58) Field of Classification Search .................... 702/19
See application file for complete search history.

(56) References Cited

U.S. PATENT DOCUMENTS 6,936,476 B1 * 8/2005 Anderson et al. ............ 436/518
2003/0033194 A1 * 2/2003 Ferguson et al. ............. 705/10

OTHER PUBLICATIONS

Danter et al., "Molecular Data Mining Tool: Advances In HIV Research", p. 31, Sep./Oct. (2000).*
"Cross Validation", J. Schneider (1997); [retrieved Aug. 2006] Retrieved from the Internet <URL:http://www.cs.cmu.edu/~schneide/tut5/node42.html>.*
Danter, et al., "Molecular Data Mining Tool: Advances in HIV Research Salford Systems", p. 31, Sep./Oct. (2000).
Kitchen, et al., "Initial Virological and Immunologic Response to Highly Active Antiretroviral Therapy Predicts Long-Term Clinical Outcome", Clinical Infectious Diseases, 33:466-472, Aug. (2001).
Miller, V., "Resistance to Protease Inhibitors", Journal of Acquired Immune Deficiency Syndromes, 26, S34-S50 (2001).
Loveday, C., "Nucleoside Reverse Transcriptase Inhibitor Resistance", Journal of Acquired Immune Deficiency Syndromes, 26, S10-S24 (2001).
Deeks, S., "Nonnucleoside Reverse Transcriptase Inhibitor Resistance", Journal of Acquired Immune Deficiency Syndromes, 26, S25-S33 (2001).
Volberding, "Introduction", Journal of Acquired Immune Deficiency Syndromes, 26, S1-S2 (2001).
Demeter, et al., "Phenotypic and Genotypic Resistance Assays: Methodology, Reliability, and Interpretations", Journal of Acquired Immune Deficiency Syndromes, 26, S3-S9 (2001).
Haubrich, et al., "Clinical Utility of Resistance Testing: Retrospective and Prospective Data Supporting Use and Current Recommendations", Journal of Acquired Immune Deficiency Syndromes, 26, S51-S59 (2001).
Arens, M., "Clinically Relevant Sequence-Based Genotyping of HBV, HCV, CMV, and HIV", Journal of Clinical Virology, 22, 11-29 (2001).
García-Lerma, et al., "Resistance of Human Immunodeficiency Virus Type 1 to Reverse Transcriptase and Protease Inhibitors: Genotypic and Phenotypic Testing", Journal of Clinical Virology, 21, 197-212 (2001).
Understanding Phenotypic Drug Resistance Testing—People Living With HIV: PhenoSense.com—"Phenotyping", p. 1-2, http://www.phenosense.com/people/331.html, printed Feb. 12, 2003.
Understanding Genotypic Drug Resistance Testing—People Living with HIV: PhenoSense.com—"Genotyping", p. 1-2, http:// www.phenosense.com/people/332.html, printed Feb. 12, 2003.
Using Both Phenotyping and Genotyping Together—People Living With HIV: PhenoSense.com—"Pheno+Geno", p. 1, http:// www.phenosense.com/people/333.html, printed Feb. 12, 2003.
Pheno Geno With PhenoSense GT—People Living With HIV: PhenoSense.com—"Pheno+Geno with PhenoSense GT", p. 1, http:// www.phenosense.com/people/313.html, printed Feb. 12, 2003.
Pheno Geno With PhenoSense GT—People Living With HIV: PhenoSense.com—"A Review of HIV", p. 1-5, http:// www.phenosense.com/people/321.html, www.phenosense.com/people/322.html, www.phenosense.com/people/323.html, www.phenosense.com/people/330.html, www.phenosense.com/people/334.html printed Feb. 12, 2003.
Horn, T., "A No-Nonsense Guide To HIV Drug Resistance Testing", pp. 1-23, (Jul. 2002).
Friedman, J., "Multivariate Adaptive Regression Splines (MARS)", Stanford Linear Accelerator Center (SLAC) PUB-4960 Rev., Tech Report 102 Rev., Aug. 1990.
Breiman, et al., "Classification and Regression Trees" Chapman and Hall/CRC New York (1993).
Http://www.salford-systems.com, "Data Mining, Web Mining, and Business Intelligence & Solutions From Salford Systems", MARS Webcast, p. 1, printed Aug. 22, 2003.
Http://www.r-project.org, "The R Project for Statistical Computing", p. 1, printed Aug. 22, 2003.
Http://www.ncbi.nlm.nih.gov, National Center for Biotechnology Information/National Library of Medicine, National Institutes of Health, NCBI HomePage, p. 1-2, printed Aug. 22, 2003.
Shafer, et al., "Human Immunodeficiency Virus reverse Transcriptase and Protease Sequence Database", Nucleic Acids Research, vol. 27, No. 1, 348-352 (1999).

(Continued)

*Primary Examiner*—Marjorie A. Moran
(74) *Attorney, Agent, or Firm*—DLA Piper US LLP (57) ABSTRACT

A method and system for deriving an outcome predictor for a data set in which a number of complex variables affect outcome. A two step model is applied that includes application of 1) a flexible nonparametric tool for modeling complex data, and 2) a recursive partitioning (e.g., classification and regression trees) methodology. In one variation, a determination is made as to whether the data set used is representative of a population of interest; if not, underrepresented data is replicated so as to produce a representative data set. In one variation, a holdout sample of the data is also used with the two step model and the determined outcome predictor to verify the predictor produced.

38 Claims, 6 Drawing Sheets

OTHER PUBLICATIONS

Http://hivdb.stanford.edu/cgi-bin/PR_Phenotype.cgi, Phenotype Query, Stanford HIV Drug Resistance Database, website, p. 1, printed Aug. 22, 2003.

Qari, et al., "Comparative Analysis of Two Commercial Phenotypic Assays for Drug Susceptibility Testing of Human Immunodeficiency Virus Type 1", Journal of Clinical Microbiology, vol. 40, No. 1, p. 31-35 (2002).

Rhee, et al., "Human Immunodeficiency Virus Reverse Transcriptase and Protease Sequence Database", Nucleic Acids Research, vol. 31, No. 1, p. 298-303 (2003).

Http://www.ncbi.nlm.nih.gov, Entreaz-Nucleotide, Human Genome, website, p. 1, printed Aug. 22, 2003.

Http://omni.ac.uk/browse/mesh/detail/C0376565L0496597.html, Anti-HIV Agents, p. 1-3, printed Feb. 12, 2003.

* cited by examiner

Continued from FIG. 5

METHOD AND SYSTEM FOR DETERMINING PHENOTYPE FROM GENOTYPE

This application claims priority from U.S. Provisional Application Ser. No. 60/361,703 filed Mar. 6, 2002. The entirety of that provisional application is incorporated herein by reference.

BACKGROUND OF THE INVENTION

1. Field of the Invention

The present invention relates to deriving an outcome predictor for a data set in which a number of complex variables affect outcome, and in particular to a method and system of derivation that includes use of a combination of a flexible nonparametric tool and a classification and a recursive partitioning methodology to model complex data.

2. Background of the Technology

There continues to be a need for improved methodologies for addressing difficulties with identifying appropriate outcome predictors for problems involving multiple complex variables potentially affecting outcome, such as are needed to accurately predict outcomes for drugs that will appropriately treat diseases.

For example, one major problem in treating Human Immunodeficiency Virus (HIV)-infected individuals is the appearance of drug-resistant strains of HIV that do not respond to therapy. Maintaining a lower "viral load" (i.e., decreasing the amount of virus in the body) is clinically beneficial both in the short and long term. There are a number of different therapeutic regimens patients may undergo that actively suppress HIV replication and thus lower viral loads. However, prolonged treatment with the currently available drugs, coupled with the relatively high mutation rates of HIV in the body can result in the appearance of drug-resistant strains of HIV. Drug resistant strains are capable of replicating in the presence of therapy, rendering therapy ineffective. This leads to higher viral loads, which in turn produce an adverse clinical prognosis.

Thus, in this example, one problem for the clinician managing the care of the HIV infected individual is developing the optimal therapeutic strategy for maintaining lower viral loads in the presence of ongoing viral mutation. In this regard, the therapeutic regimen may be changed following the emergence of drug-resistant HIV to a more efficacious regimen to which there is not pre-existing resistance that lowers viral loads.

There are various known mutations in the HIV genome that are associated with drug resistance, yet there remains no reliable quantifiable method in the prior art to predict how these mutations will affect the degree to which the virus evades drug therapy. The information derived from viral genotype testing is extremely complex. It is generally not possible to determine an optimal treatment strategy from this data because, for example, the degree of drug resistance and cross-resistance to other drugs is difficult to infer. Cross-resistance in this example is defined as pre-existing resistance of a virus to a drug that has not been taken due to a mutation induced by another drug that has already been taken. This phenomenon primarily occurs because many drugs are very similar to each other and target the same sites in the viral proteins.

There remains an unmet need to provide methods and systems for accurately predicting outcomes to problems having multiple complex variables. For example, there remains an unmet need to provide methods and systems for predicting treatment outcomes, such as drug response, for diseases involving numerous complex variables.

SUMMARY OF THE INVENTION

The present invention provides a method and system for deriving an outcome predictor for a data set in which a number of complex variables affect outcome, also referred to interchangeably herein as "determining genotype from phenotype." In one embodiment, a two step model is applied that includes application of 1) a flexible nonparametric tool for modeling complex data (e.g., Multivariate Adaptive Regression Spines or MARS), and 2) a recursive partitioning methodology (e.g., a classification and regression trees (CART) methodology). In one embodiment, basis functions for interactions among the variables are generated using MARS, rules are determined for the generated basis functions, and CART is applied to the data set to produce an outcome predictor, using the determined rules.

One embodiment includes initial determination as to whether the data set to be used with the outcome predictor derivation is representative of a data population of interest (e.g., the set of data for individuals in a disease group is representative of the overall population of individuals of interest). In this embodiment, if the initial data set is determined not to be representative, underrepresented data is appropriately replicated and the replicated data combined with the data in the initial data set so as to produce a resulting modified data set that is representative of the data population of interest. Further, as appropriate, the present invention includes use of publicly available and other sources of information to verify whether the data set is representative.

In one variation, a holdout sample of the data is also used with the two step model and the determined outcome predictor (produced using the remaining non-holdout data, referred to interchangeably herein as a "training sample") to verify the predictor produced.

The present invention is particularly applicable for, but not limited to, determining effectiveness of medical treatment (e.g., drug effectiveness) for particular conditions, such as diseases. In one embodiment for medical treatment application, a determination is first made as to whether the genetic and other data for a population being studied (e.g., for which data is available) is representative of the general population of concern (e.g., population for which treatment is potentially applicable). If the data is not representative, rare types of data in the population (i.e., data that are underrepresented) are replicated and added to the initial data set, so as to produce an accurate representative population.

In one embodiment, a percentage of the data from the representative data set are then withdrawn as a holdout sample for later use with model verification. The remaining portion of the representative data set is then modeled using a two step process. In a first step, the data is used in MARS to create rules for aspects of the interactions among data involved (e.g., mutation combination possibilities for HIV produce rules for the codons involved). MARS generates basis functions in the form of a single variable transformation or multiple variable interactions, which are then used to produce rules constructed for use in the second step, CART modeling. For example, in one embodiment, the rules used in CART are programmed using a programming language, such as, but not limited to, BASIC, C, S$^+$, Fortran, Cobal, Pascal, or Java, based on the basis functions generated by MARS. The rules may also be varied via analysis of publicly available or other information relating to the data interactions (e.g., additional mutation interactions may be known from published literature).

CART is then run for a target treatment (e.g., drug) as the target variable using the above generated rules. CART produces an output predictor, such as decision tree results, for each genotype (e.g., drug resistance). The treatment results are then validated via the MARS and CART modeling using the withdrawn holdout sample data set.

In one embodiment, the method is partially or wholly performed in an automated manner using a system that includes a processor, such as a personal computer (PC) or, for example, a PC coupled to a server on a network.

Additional advantages and novel features of the invention will be set forth in part in the description that follows, and in part will become more apparent to those skilled in the art upon examination of the following or upon learning by practice of the invention.

DETAILED DESCRIPTION

The present invention provides a method and system for deriving an outcome predictor for a data set in which a number of complex variables affect outcome. In one embodiment, data is modeled to produce the outcome predictor using 1) a flexible nonparametric tool, such as MARS, and 2) a recursion partitioning methodology, such as a CART methodology, as described further as follows:

1. Flexible Nonparametric Tool

MARS, one representative example of a flexible nonparametric tool usable for modeling with the present invention, was developed by Jerome Friedman in his paper entitled "Multivariate Adaptive Regression Splines," (1991), which was published in 19 Annals of Statistics, 1-141. MARS contains a nonlinear, nonparametric function that can handle large amounts of data. Whereas recursive partitioning (RP), as described further below, uses binary decision trees, MARS fits regression models. Exemplary MARS software is available at http://www.salford-systems.com. MARS is also widely used in data mining in the same applications in which RP is used. MARS is more flexible than RP in that flexible piece-wise linear functions are fit, rather than the binary split method (step functions) of RP being used. That is, MARS can fit approximate any form of a surface by utilizing a piece-wise linear function.

MARS thus provides a flexible nonparametric tool to model non-linear or complex data. In operation, because MARS finds optimal variable transformations in building a piecewise linear predictive regression function, weighted predictors become smooth functions of the outcome. This is in contrast to the step-function of RP, in which a small change in a predictor can produce large changes in the outcome (e.g., tree structure). Because of its flexible nature, MARS has high stability and has the ability to detect complex or hidden interactions within data. This is achieved by overfitting the data by utilizing piecewise linear regression functions to the data, and pruning back, based on a mean squared error criterion, as known in the art. However the interpretation of the resulting model can be difficult.

2. Recursive Partitioning

RP, such as CART, is a well-known methodology useful for constructing outcome predictors, such as decision frees. The methods used in RP work well for both binary and continuous data. Software for RP is available, for example, through the package RPart in the software R, which is freely distributed at r-projeet.org on the World Wide Web. R, also known as 'GNU S', is a freeware system for statistical computation and graphics similar to S-plus, as is known in the art. CART was first developed in L. Breiman, Jill. Friedman, A. Olshen, and C.J. Stone. *Classification and Regression Trees*. Chapman and Hall, New York (1993).

RP is a nonlinear, nonparametric method known in the art that allows evaluation of large amounts of data and detection of patterns in the data. RP is widely used in data-mining applications, such as for credit risk prediction, customer profiling, direct-marketing strategies, and quality control. With RP, the patterns are transformed into a binary decision tree, which allows the output to be interpreted easily. RP accomplishes this transformation by relying on a strategy that includes separation of the data into two groups. RP exhaustively analyzes all possible splits (e.g., break points for the data) and each split that has a higher purity (i.e., fewer mistakes) is retained.

For example, in a study on heart disease, CART may analyze age as a variable for splitting. RP identifies all possible age splits and identifies, for example, 20 as the age break point. That is to say, that patients less than 20 do not have heart disease and patients greater than 20 have heart disease. RP then identifies additional variables for which to select break points, such as family history.

One problem with CART is that the produced decision trees may be unstable, and accuracy can be compromised when CART is used on its own. Since accuracy is one important objective of the present invention, a method is needed for incorporating the ease of interpretation of CART with more stable methods. The present invention addresses this problem via use of recursive partitioning, such as CART, in conjunction with a flexible nonparametric tool, such as MARS.

Example Application to HIV Treatment

The following example presents use of the present invention for an application to outcome prediction relating to drug treatment for HIV. The example is not intended to be limiting, but merely illustrative of one application of the present invention for medical treatment outcomes.

In this example, the method and system of the present invention allow use of the viral genotype of an HIV infected individual, which is currently a common test performed in the clinic, to predict the degree of resistance ("phenotype") the predominant virus in the blood will have to each of the currently available drugs. The method and system of the present invention, and the subsequent information derived from its results, is usable, for example, by physicians as a guide for developing a personalized treatment strategy based on the genotype of the predominant virus in the blood.

The patient database used for modeling in this example includes patients who are antiretroviral drug experienced (i.e., those who have taken one or more antiretroviral drugs). The data includes genotypic analysis of the nucleic acid sequences in the HIV-1 polymerase gene (e.g., the protease (PR) and reverse transcriptase (RT) portions of the polymerase gene, which are two targets of antiretroviral drugs), coupled with phenotypic analysis of viral growth in the presence of a drug, performed in tissue culture. The genotypic analysis yields the linear sequence of nucleotides (A, T, C, or G), with each triplet of nucleotides, called a codon, specifying which amino acid residue is incorporated at the corresponding position in the protein. Thus, genotypic analysis identifies the presence of codon mutations in a patient's virus population by identifying codons that differ from the "wild-type" (i.e., non-mutant virus or standard). By convention in the art, a "codon position" is understood to represent the position of the amino acid within a polypeptide (e.g., the first three nucleotides constitute codon 1, which in turn, specifies the first amino acid in the polypeptide).

An identification of mutations can be produced by comparison of known sequences of these genes, as well as comparison of sequences that are known to be associated with drug resistance. The phenotypic analysis indicates how well a virus with a specific nucleic acid sequence derived from the patient will grow in tissue culture in the presence of different drugs, in comparison to a wild type virus. In one embodiment, as is known in the art, this comparison generates a number between 0 and 500 that is known as the "fold-resistance" to the drug.

In one embodiment, fold-resistances that are between 0 and 1 are considered "hypersensitive"; that is these viral strains are more susceptible to drugs than their wild-type counterparts. Fold-resistances between 1 and 2.5 are generally not considered significantly drug-resistant. Although virus strains with fold-resistances between 2.5 and 10 are generally considered drug-resistant, no specific criteria has been established for these strains. Scores over 10 have high-levels of drug-resistance.

Different mutations in different codons of the target gene produce different phenotypic fold-resistances. Although a specific genotype may suggest drug resistance or susceptibility, the phenotypic analysis of the present invention is capable of indicating the degree to which a specific virus with a defined gene sequence is resistant or susceptible to a particular drug. One statistical problem solved by the present invention lies in performing the function of coupling this data together and determining the relationship between a specific sequence and the fold-resistance.

Drugs Used in Example Application for HIV

In this example, anitiviral drugs with which the present invention is used for determining effectiveness for HIV treatment include those currently approved for such treatment, such as certain drugs listed as nucleoside reverse transcriptase inhibitor (NRTI) class drugs, those listed as non-nucleoside reverse transcriptase inhibitor (NNRTI) class drugs, those that are Protease Inhibitors (PIs), and Combination Drugs. These drugs include, but are not limited to, the following:

a. NRTI Class

This class of drugs targets the reverse transcriptase region (RT) of HIV-1 polymerase (pol). These drugs are analogs of naturally occurring deoxyribonucleosides and inhibit synthesis of viral deoxyribonucleic acid (DNA) at the early stages of infection of a cell by competing with the natural substrate and also by their incoporation into the viral DNA. For use in this example, the drugs in this class include: 1) Abacavir (ABC); 2) Adefovir (ADV); 3) Didanosine (ddI); 4) Lamivudine (3TC); 5) Stavudine (d4T); 6) Tenofovir (TDF); 7) Zalcitabine (ddC); and 8) Zidovudine (AZT, ZDV).

b. NNRTI Class

These drugs, which target the RT region of HIV-1 pol, inhibit the synthesis of viral DNA by blocking RT and polymerase activity. For use in this example, drugs in this class include: 1) Delavirdine (DLV); 2) Efavirenz (EFV); and 3) Nevirapine (NVP).

c. PI Class

These drugs target the protease (PR) region of the HIV-1 pol. The PIs block the processing of viral proteins and prevent the maturation of virus into infectious particles. These drugs target the viral life cycle at its latest stages. For use in this example, drugs in this class include: 1) Amprenavir (APV); 2) Atazanavir (ATV); 3) Indinavir (IDV); 4) Lopinavir (LPV); 5) Nelfinavir (NFV); 6) Ritonavir (RTV); and 7) Saquinavir (SQV).

d. Combination Drugs

Current patient drug regimens require that several drugs be taken at one time. Several drugs are currently available that combine compounds from the NRTI class. For use in this example, drugs in this class include the following: 1) Trizavir (AZT, 3TC, ABC); and 2) Combivir (AZT, 3TC).

Data Used in Example HIV Application

In this example, for genetic or drug-related application, the present invention includes use of certain sequence data, such as a nucleotide sequence that has been translated into the corresponding amino acid sequence. This information provides all of the nonsynonomous mutations. Synonomous mutations are not likely to change the structure of the molecule and hence will not affect resistance. Thus, this example is confined to only the nonsynonomous changes in the genome. The method and system of the present invention, when used with this example, analyze point mutations, but also allow for insertions and deletions, as well as frame-shift mutations. These mutations are not applicable, however, in the present example. As mixtures of amino acids signal continued evolution in that position, mixtures in this example were considered as mutants.

In developing a methodology specific to the present exemplary application, consideration was given to the fact that, when linking genotype with fold-resistance, in the clinical setting, false negatives (those sequences that are falsely deemed retroviral drug resistant) are especially worrisome since there are a limited number of antiretroviral agents available. For instance, it would be potentially detrimental to say that a patient is infected with a virus that is resistant to a certain antiretroviral drug, when in fact the virus is sensitive. Because of this false negatives concern, over-sampling of the low resistance phenotype was performed.

Use of Modeling for Data in Example Application

One problem with analysis for this example application of the present invention is that genotypic data is often troublesome to work with because more predictor variables (possible mutations) are available than are observations (number of full genotypes). This leads to problems with estimation and identification of the parameters of interest. To address this problem, as well as others, one embodiment of the present invention combines MARS and CART so as to reduce the dimensionality of the problem.

For example, returning to the HIV example, in protease there exist 99 codon positions. If all possible interactions of the codon positions were to be examined, 99! (greater than $9^{155}$) parameters would result. This clearly cannot feasibly be performed in any real-time analysis. A reliable method is needed to reduce the dimensionality of the problem so that the model of the present invention may be estimated. In one embodiment, this is accomplished by initially deleting mutations that do not occur in vivo, as follows:

1) HIV-1 DNA sequences in the National Library of Medicine's Genebank (located at http://www.ncbi.nlm.nih.gov), which contains a large public database of HIV-1 sequences, are examined, If no mutations exist in a given codon position, then that mutant and all of its interactions are dropped from the analysis. This greatly reduces the parameter space. Correlation studies on the condon positions are also important for other reasons, such as to detect mutational patterns and interactions.

2) A pairwise correlation analysis is conducted on all possible pairs of codon positions.

3) A 3-way codon correlation analysis is performed.

4) Previously published work on site-directed mutagenesis and other genotype-phenotype correlative studies are reviewed to determine some of the important mutation interactions. Since, for example, MARS produces good results in detecting interactions, a MARS analysis is conducted on the data first to detect interactions among the various codons. A flexible nonparametric tool, such as MARS, is valuable with regard to this analysis aspect, as MARS allows for mutation interactions for up to 7-fold interactions.

In this example, using all four methods above, "rules" are developed for the codons. That is, a priori a determination is made as to what mutation combinations are expected to be important. This determination produces a reduced parameter space. For example, instead of including all 99! parameters as possible predictors in CART, only the point mutations that are seen in vivo (e.g., that are established from Genebank), as well as all of the mutational interactions that are obtained from the literature, MARS modeling, and correlation analysis, are included in the analysis. This reduced parameter approach is programmed (e.g., coded in BASIC) within a recursive partitioning methodology, such as CART. Then CART is run using the a priori predictors to produce the resulting outcome predicotrs (e.g., decision trees).

In this example, the present invention combines the techniques of MARS and CART so as to obtain the stability and accuracy of MARS, with the ease of interpretation of CART. First, a MARS analysis is conducted and the predictors and the interactions are obtained. Then the predictors and their interactions are input into CART. This combination of modeling results in a dramatic decrease in the dimensionality of the problem and greatly increases the accuracy of the resulting decision trees that are generated. As a result, stable trees with high degrees of accuracy are produced, which are far better than those generated by bagging, arcing, kernel regression, and other methods designed to increase tree stability.

Development of Representative Data Set for Example Application

In the HIV example, the database on which the analysis is based includes data from patients for whom clinicians specifically ordered the phenotype test and data obtained from clinical trials. Since this database is not comprised of data derived from a random sample of a representative population of all HIV-infected patients, it has the potential for selection bias. In fact, most clinicians order the phenotype test either shortly after primary infection or after a patient fails a therapeutic regimen. Because of this, one could expect that virus with low resistance or moderate resistances would be under-represented in this sample population (i.e., a selection bias results).

The construction of a frequency histogram of the phenotypes can provide insight into the extent of the selection bias. That is, a frequency histogram could be constructed for the number of mutations at each codon position for the entire sample. For instance, how many times does a mutation appear at codon position 10? A frequency histogram can also be produced for the phenotype. For this example, it was expected that in large samples, a distribution that vaguely resembles the normal distribution would result.

In the particular dataset of the HIV example, there are relatively fewer patients that have low or moderate resistance (e.g., phenotypes with fold-resistance from 0-8). Since, in the example, the preference is to err on the side of over-inclusion of this characteristic, this "rare" phenotype is oversampled. This oversampling helps overcome the selection bias. To accomplish this oversampling, rare phenotype-genotype pairs are replicated with replacement until these rare types account for approximately 20% of the entire database. Replicating with replacement as used in this example means that there is a possibility that a phenotype-genotype pair may be replicated more than once.

Once a near representative database is produced, a predetermined amount (e.g., 25% in this example) are withheld from the database as a "holdout sample." This holdout sample of data is maintained separately from the remaining portion (e.g., 75% in this example) of the data, which is referred to interchangeably herein as the "training sample." The holdout sample is used following development of the decision trees to test the validity of the trees. The method of modeling using MARS and CART is conducted on the training dataset only.

In this HIV example, the data were obtained at hivdb.stanford.edu, at which is located a database maintained by Robert Shafer, M.D., which contains a compilation of nearly all of the published phenotype-genotype pairs known in the literature (see, e.g., Robert W. Shafer, Derek Stevenson, and Bryan Chan, "Human immunodeficiency virus reverse transcriptase and protease sequence database," 27(1) *Nucleic Acids Research* 348-352 (1999)), each of which are hereby incorporated by reference. Specifically, in this example, at the Website hivdb.stanford.edu/cgi-bin/PR_Phenotype.cgi (information at which is hereby incorporated by reference), each drug and the assay was selected, and a database query was performed, which produced all phenotype/genotype pairs for each drug. Data generated from assays by Tibotec-Virco, Inc., of Durham, N.C., and Virologic, Inc., of South San Francisco, Calif., were selected, as these assays are commercially available and have proven consistency. (See, e.g., "Comparative analysis of two commercial phenotypic assays for drug susceptibility testing of human immunodeficiency virus type 1," 40(1) *Journal of Clinical Microbiology* 31-5 (January 2002), which is hereby incorporated by reference).

Method of Operation for HIV Example

The method of operation for the HIV example, in accordance with an embodiment of the present invention, is thus as follows:

Step 1: Identify all phenotypes with a fold-resistance from 0-8 (those considered the rare phenotype) separately for each drug, for example, Indinavir. (Note: this step must be performed on genotype-phenotype pairs). Replicate with replacement until the rare phenotype is at least 20% (for this example) of the total number of available sequences. This assumes that these rare phenotypes in the sample are representative of this population. The full data set is then complete. Randomly select 25% (for example) of the data as a holdout sample which will be used to test the trees produced following modeling. The remaining 75% ("training data") are used in the actual modeling.

Step 2: Set the options of the MARS program as follows:
 a. Accuracy options=most accurate (for example, if selectable range is between 1 and 5, with 1 being the most accurate, 1 is selected).
 b. Max basis functions=200
 c. Interactions=7 fold-interactions.
 d. Minimum observations between knots=0.

These settings are for illustrative purposes only. For refinement purposes, other settings may be optimal.

Run MARS on the "training sample."

Step 3: Use the "training sample" output from MARS to create rules for mutations. MARS generates basis functions in the form of a single variable transformation or multiple variable interactions. MARS provides excellent results for identifying interactions between variables in sparse datasets.

Step 4: Construct rules for CART. Turn the basis functions produced by MARS into "rules." In one embodiment, the "rules" are programmed into the CART software using BASIC, but the present invention is not restricted to this language. In BASIC, for example, if it is known that there is an interaction between codon 48 and codon 82, a code line could be written to address this interaction, as follows: "if codon 48=1 and codon 82=1 then mutant 48 82=1 else=0." This code line would thus select for all sequences that have saquinavir resistance mutations in the protease gene at both the codon 48 and the codon 82 positions.

In this example, MARS generates most of these "rules" for coding from the data described above; however, it is important to make sure to include all known mutation interactions, including exceptions to general mutations identified by the modeling results produced by MARS (e.g., 184 mutation and the 215 mutation in RT are known, but all of these may not be generated by MARS modeling). To address any additional known mutations, further rules are added to CART, as appropriate.

The known mutations can be obtained, for example, from a wide variety of public information sources, such as the extensive literature on mutations. A 2- and 3-fold correlational analysis is constructed, and the mutations that correlate are entered into the "rules" for CART. All of this is performed to reduce the dimensions, or possible parameters. Once these rules are programmed into the BASIC language of CART, CART may be run.

Step 5: CART is run: a target drug (e.g., Indinavir) is selected as the target variable and all the "rules" set above are provided as the predictors. These settings create the resulting decision trees.

Step 6: Validate the results on the hold-out sample.

Step 7: CART produces decision trees for each genotype (in this case, each drug). These are general enough to use for the population being studied. The decision trees provide, for each terminal node, the expected fold-resistance for each genotypic sequence (e.g., drug), given a phenotype. This is easy to interpret and accurate. (For examples of the CART-generated trees, see FIGS. 5 and 6 and accompanying description below.)

Other Applications of the Present Invention

The methodology of the present invention has many other practical uses than for treatment analysis for HIV. For example, this methodology is usable to predict in clinical trials whether a subject is likely to be a placebo responder. That is, is the subject as likely to respond to a placebo as to respond to a given drug? The ability to identify these patients before the start of a trial could potentially save time and money, as well as detect the true effect of the drug under investigation. Further, this methodology could be used to identify genetic factors that render individuals susceptible to a variety of inherited and acquired diseases, as well as to develop drug resistance profiles that result from treating these ailments.

Moreover, this methodology could be applied to anything that has many variables, genetic or phenotypic, and a single or limited corresponding phenotype or genotype, respectively. For example, investigators believe that certain regions of the brain grow faster in people diagnosed with autism at young ages than normal people. This rapid growth then dramatically slows down over time in autistic individuals. It is also believed that certain regions or the brain are more involved in the development of autism than others. From brain mapping/imaging studies, many variables are generated regarding the brains of autistic individuals, with one phenotypic outcome: autism disease. This methodology can be used to sort out variables that lead to the development of autism. In this way, it may be possible to predict early on which individuals are more susceptible to autism. More broadly, this methodology can be employed to predict a single variable from multiple variables in many different areas, including but not limited to the medical, behavioral, biologic, physical, engineering, and economic sciences, as well as in marketing and business. For example, in the medical field this could include such disease areas as Acquired Immune Deficiency Syndrome (AIDS), infectious diseases, blood diseases, hepatitis, heart disease, diabetes, epilepsy, cancer, mental disorders, neurological disorders, liver disease, urological disorders, kidney disorders, congenital defects, and many other medical conditions.

This methodology is generally beneficial in deriving the relationship between one continuous outcome variable with many predictors. Current methods often fail when there are many more parameters (explanatory variables) than there are observed data. The method and system of the present invention can overcome the identification problem by reducing the dimension of the parameter space and identifying important interactions.

The trees generated by the use of MARS and CART in this manner serve as one result of the present invention. These trees can further be used in software and in other forms to yield interpretable data. In the case of HIV drug resistance, for example, the resultant decision trees generated by this methodology could be used to generate a clinical report that is provided to physicians to aid in developing optimal treatment strategies for HIV infected individuals. In other cases, the trees could be used for such purposes as: brain mapping (e.g., using data from Positron Emission Tomography (PET) scans or functional Magnetic Resonance Imaging (fMRI)) and identifying factors that lead to schizophrenia, depression, head trauma, autism, etcetera; genetic mapping studies such as gene and environment interactions; and, mass marketing studies of given products.

References will now be made in detail to embodiments of the present invention, examples of which are illustrated in the accompanying drawings.

Figure 1:
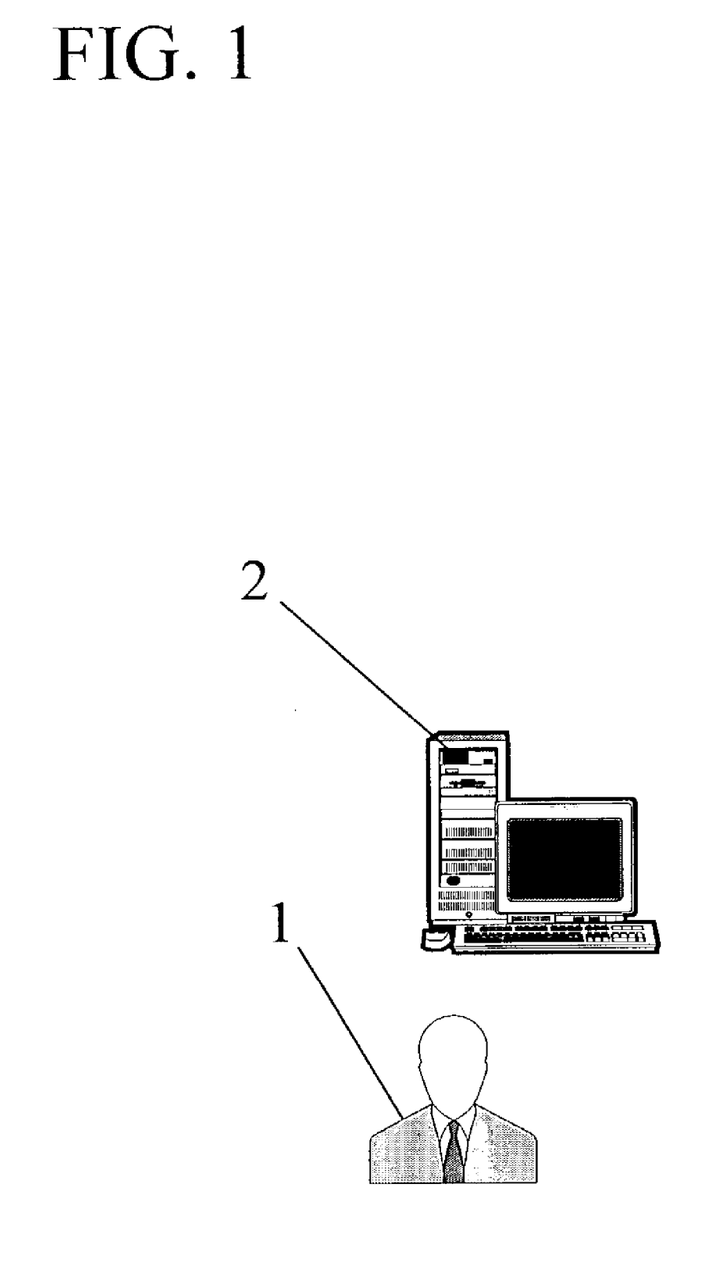
FIG. 1 presents various components of a standalone system for deriving an outcome predictor for a data set having a plurality of variables affecting outcome, in accordance with an embodiment of the present invention.

As shown in FIG. 1, in an embodiment of the present invention, modeling is performed by a user 1 via a terminal 2, such as a PC, minicomputer, mainframe computer, microcomputer, telephonic device, or wireless device, such as a handheld wireless device (e.g., PDA), and all input, processing, and data access occurs via the terminal 2.

Figure 2:
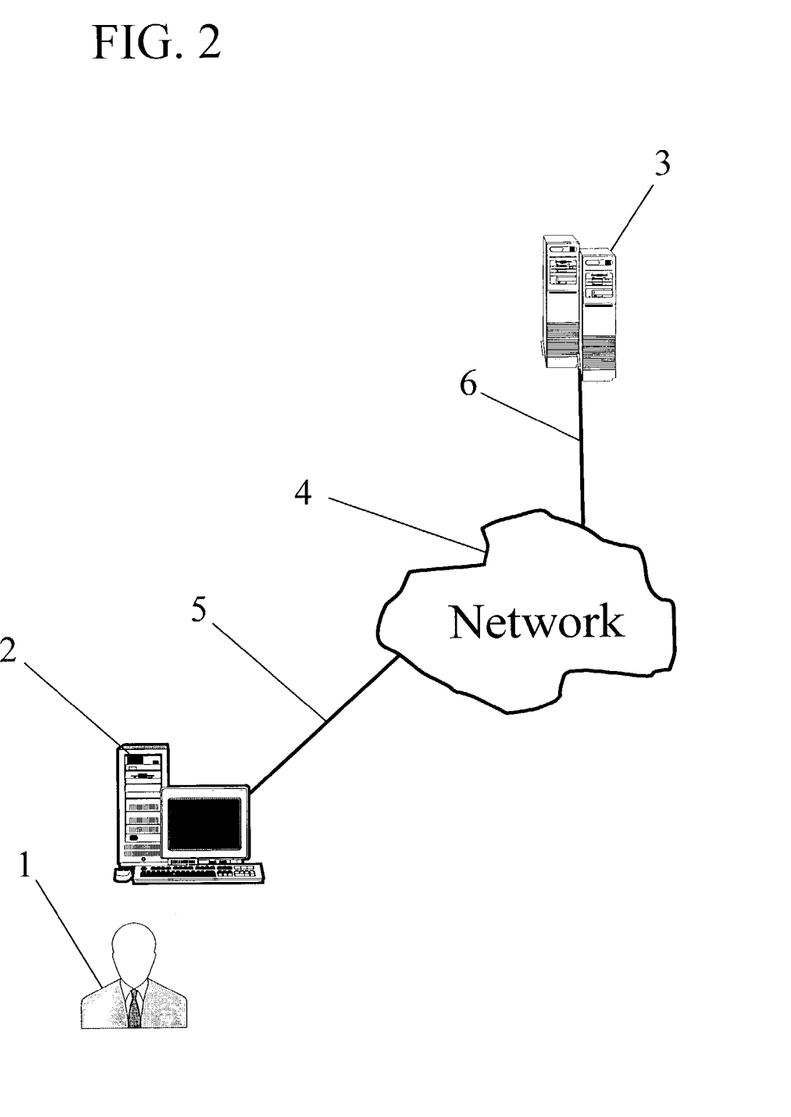
FIG. 2 shows the components of a network-based system for deriving an outcome predictor for a data set having a plurality of variables affecting outcome, in accordance with an embodiment of the present invention.

In a second embodiment, as shown in FIG. 2, modeling is performed by a user 1 via a terminal 2 coupled to a server 3, such as a PC, minicomputer, mainframe computer, microcomputer, telephonic device, wireless device, or other device on a network 4, such as the Internet or an intranet. The terminal 2 can, for example, have or be accessible by a processor and/or have or be coupled to a repository for data via the network 4, and couplings 5, 6. The couplings 5, 6 include, for example, wired, wireless, or fiberoptic links.

Figure 3:
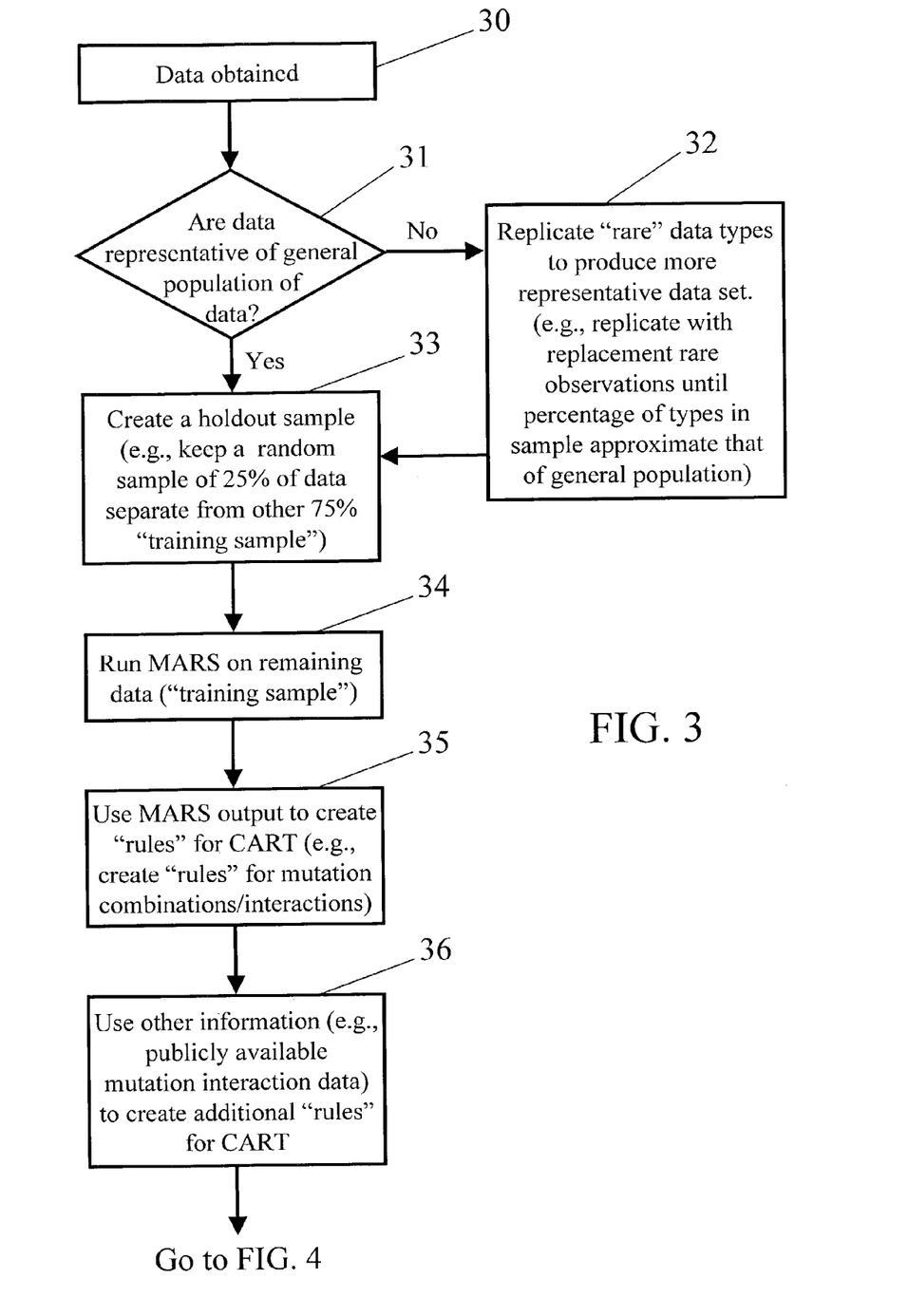
FIGS. 3 and 4 contain a flow chart of an overview of a method for deriving an outcome predictor for a data set having a plurality of variables affecting outcome, in accordance with an embodiment of the present invention.
Figure 4:
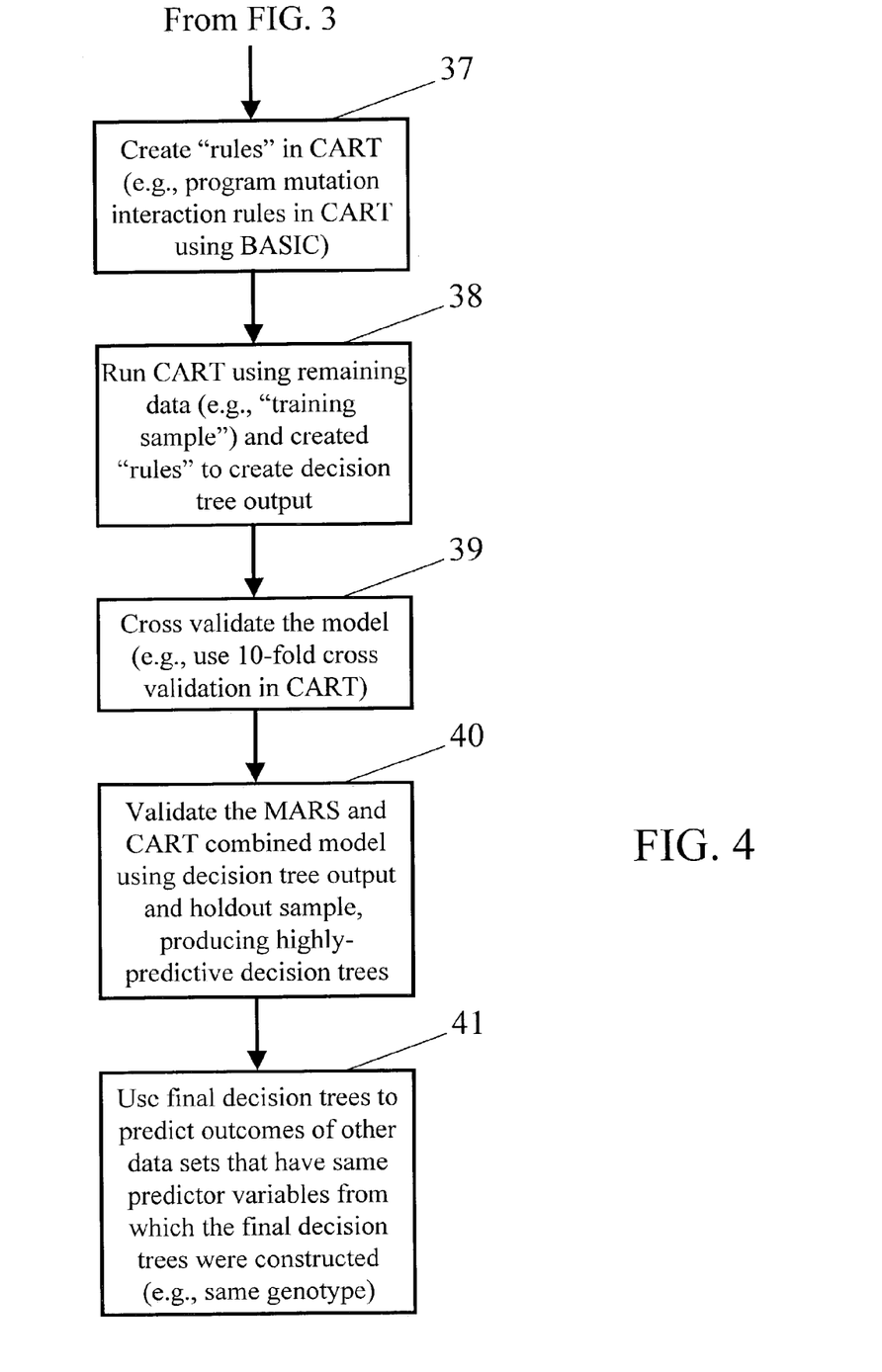

FIGS. 3 and 4 contain a flow chart of an overview of a method for deriving an outcome predictor for a data set having a plurality of variables affecting outcome, in accordance with one embodiment of the present invention. As shown in FIG. 3, a data set for which the outcome predictor is to be derived is first obtained 30. A determination is then made as to whether the data set is representative of a general population of data for which the outcome predictor is to be derived 31. If not representative, in one embodiment, a representative data set is produced 32, such as by replicating and adding to the data set "rare" data types so as to produce a new, more representative data set containing the original data in the data set and the replicated data. For example, rare observed data in the data set are replicated until the percentage of these types in the revised data set approximate the appropriate percentage of these data in the general population.

If the initial data set is determined to be representative 31, or once a representative data set is produced 32, a holdout sample is created 33. For example, the holdout sample may be produced by randomly withdrawing a predetermined percentage (e.g., about 25%) of the data from the representative data set and holding this holdout sample of data aside (e.g., creating two data sets from the representative data set, a first holdout sample of about 25% of randomly selected data from the data set and a second "training sample" of about 75% of the remaining data from the representative data set).

Modeling using a flexible nonparametric modeling tool (e.g., MARS) is then performed on the "training sample" data set 34. Output (e.g., a set of basis functions) is produced by the flexible nonparametric modeling tool, which, in turn, is usable for developing "rules" for use with CART. For example, for use with the HIV drug modeling example above, the rules may relate to mutation combinations or interactions applicable to the analysis. Other information is then also identified, as appropriate, for use to create further "rules" for use with CART 36. For example, for the HIV drug modeling example, additional rules may be produced for use with CART using publicly available information on mutation interaction (e.g., certain unexpected mutations found).

As shown in FIG. 4, the output of the flexible nonparametric modeling tool and any identified additional information are then used to produce "rules," such as by coding in a programming language, within a CART model 37. For example, with the HIV example above, mutation interaction rules may be programmed in a programming language, such as BASIC. The CART model is then run using the "training sample" data and the input "rules" to produce an outcome predictor, such as a decision tree output 38. The modeling is also cross validated 39 (e.g., 10-fold cross validation is used within CART).

The overall model of the present invention is also validated using the outcome predictor and the holdout sample data, which produces highly predictive outcome predictors, such as decision trees 40. The final outcome predictor (e.g., decision trees) are optionally also usable to predict outcomes for other data sets that have the same predictor variables from which the outcome predictor is produced 39. For example, new data of the same genotype as the data used in the modeling may be used with the produced outcome predictor to predict outcomes for this new data.

Figure 5:
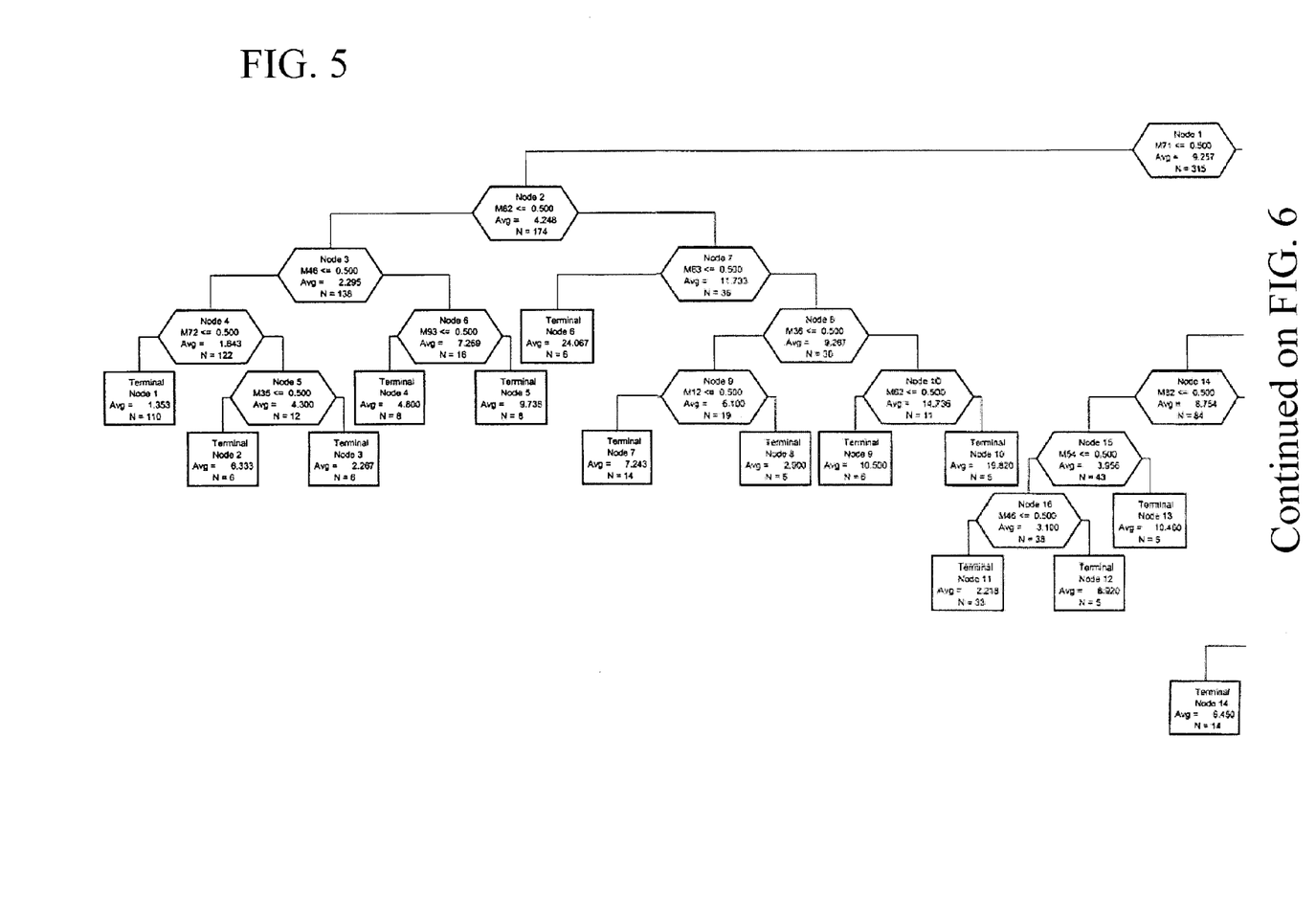
FIGS. 5 and 6 show an example decision tree output for a data set having a plurality of variables affecting outcome, in accordance with an embodiment of the present invention.
Figure 6:
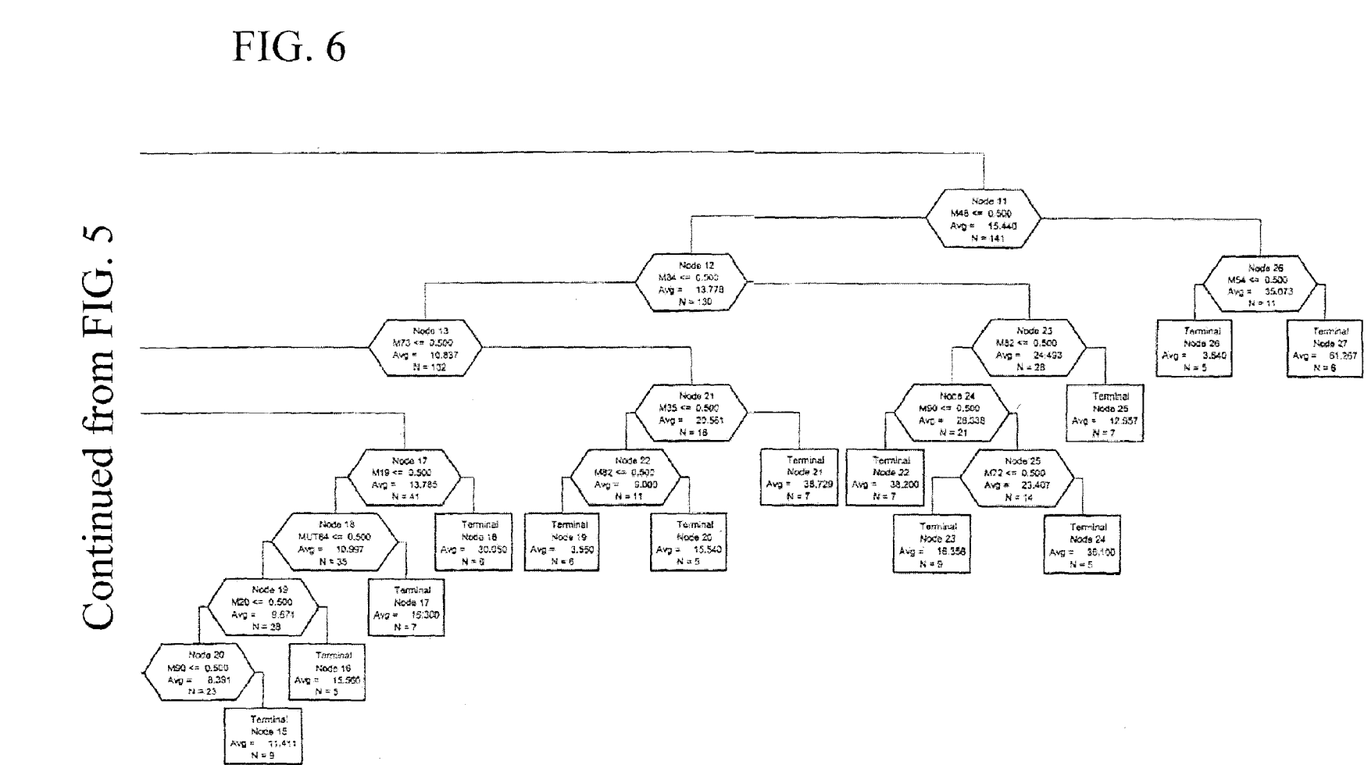

FIGS. 5 and 6 show an example decision tree output for a data set having a plurality of variables affecting outcome, in accordance with an embodiment of the present invention. Appendix A Example embodiments for the present invention have now been described in accordance with the above advantages. It will be appreciated that these examples are merely illustrative of the invention. Many variations and modifications will be apparent to those skilled in the art.

APPENDIX A

Figure Legend for FIGS. 5 and 6

The simple tree generated using the genotype/phenotype methodology for the drug Indinavir, shown in FIGS. 5 and 6, can be read as follows:

One starts with the first node, labeled Node 1. Node 1 is M71. The node states M71<=0.500. This reads as: if there is NO mutant at codon position 71, that is M71=0, then follow the tree to the left to Node 2. If there is a mutant at position 71 (M71=1), then follow the tree right to Node 11. Thus, if there is no mutation at position 71, proceed to Node 2. Node 2 states that M82<=0.500. This reads: if there is no mutation at position 82, then go left to node 3, else go to the right to Node 7. Thus, if there is no mutation at position 82, proceed to Node 3.

Node 3 states that M46<=0.500. This reads as: if there is NO mutant at codon position 46 (M46=0), then follow the tree to the left to Node 4. Thus, if there is a mutant at position 46 (M46=1), the tree is followed right to Node 6. If there is no mutation at position 46, proceed to Node 4. Node 4 is M72<=0.500. This reads as: if there is NO mutant at codon position 72, then follow the tree to the first terminal node, Terminal Node 1.

Terminal Node 1 states that for patients who do not have mutations at positions 71, 82, 46, or 72, then the average fold resistance is 1.353. The clinical cutoff for Indinavir in this example is greater than 2.5, so this patient would be deemed susceptible to Indinavir. The other nodes can be read similarly.

As shown in the example of FIGS. 5 and 6, the terminal nodes are the nodes that provide the predicted fold resistance, given the genotype. The genotype, in this example, is the series of mutations at each position in the tree. Thus, for any given genotype, the tree in this example provides the predicted fold resistance.

What is claimed is:

1. A method for deriving an outcome predictor for a data set, wherein a plurality of variables affect outcome for the data set, the method comprising:
   randomly selecting a holdout sample from the data set;
   withdrawing the holdout sample from the data set, such that a remainder data set and a holdout data set are created;
   generating basis functions for interactions among the plurality of variables for the data set using Multivariate Adaptive Regression Splines;
   determining rules for the generated basis functions relating to the interactions among the plurality of variables;
   applying a Classification and Regression Trees recursive partitioning methodology to the data set, using the rules determined for the generated basis functions, to produce the outcome predictor; and outputting the outcome predictor.

2. The method of claim 1, further comprising:
verifying the outcome predictor.

3. The method of claim 1, further comprising:
identifying non-data set related rules applicable to the interactions among the plurality of variables;
wherein applying the Classification and Regression Trees recursive partitioning methodology further includes using the identified non-data related rules.

4. The method of claim 1, wherein the data set is developed from an initial data set, the method further comprising:
determining whether the initial data set is representative of a population of data, the initial data set being a subset of the population of data; and
if the initial data set is not representative of the population of data, identifying underrepresented data in the initial data set, and replicating and adding the underrepresented data to the initial data set, such that the data set produced is representative of the population of data.

5. The method of claim 4, wherein determining whether the initial data set is representative of a population of data includes comparing data in the data set to publicly available information relating to the data.

6. The method of claim 4, further comprising:
if the initial data set is representative of the population of data, using the initial data set as the data set.

7. The method of claim 1, wherein the holdout sample includes approximately 25% of the data set.

8. The method of claim 7, wherein the data set is a representative data set.

9. The method of claim 1, further comprising:
applying the outcome predictor to a second data set.

10. The method of claim 9, wherein the plurality of variables affecting outcome for the data set affect outcome for the second data set.

11. The method of claim 1, wherein the basis functions are generated in a single variable transformation format.

12. The method of claim 1, wherein the basis functions are generated in a multiple variable interactions format.

13. The method of claim 1, wherein the basis functions are generated in a programming language.

14. The method of claim 13, wherein the programming language is selected from a group consisting of BASIC, C, $S^+$, Fortran, Cobal, Pascal, and Java.

15. The method of claim 1, wherein generating basis functions for interactions among the plurality of variables for the data set includes:
modeling data in the data set.

16. The method of claim 1, wherein the data set includes genotypic data.

17. The method of claim 16, wherein the outcome predictor is used to determine a personalized treatment regimen for an individual.

18. The method of claim 17, wherein the individual has Human Immunodeficiency Virus (HIV).

19. The method of claim 1, wherein the data set includes phenotypic data.

20. The method of claim 1, wherein the outcome predictor comprises a decision tree.

21. The method of claim 1, wherein the outcome predictor comprises a decision tree for a clinical report for a physician.

22. The method of claim 1, wherein the outcome predictor comprises a decision tree liar use for a genetic mapping study.

23. The method of claim 22, wherein the genetic mapping study is used to determine gene and environment interactions.

24. The method of claim 1, wherein the outcome predictor comprises a decision tree for use for a mass marketing study for a product.

25. The method of claim 16, wherein the outcome predictor comprises a decision tree relating the genotype information to at least one treatment type.

26. The method of claim 25, wherein the at least one treatment type includes an administered drug.

27. The method of claim 1, wherein the outcome predictor is used to determine a personalized treatment regimen for an individual.

28. The method of claim 27, wherein the individual has a disease.

29. The method of claim 28, wherein the disease is selected from a group consisting of autism, Acquired Immune Deficiency Syndrome (AIDS), a blood disease, hepatitis, heart disease, diabetes, epilepsy, cancer, a mental disorder, a neurological disorder, liver disease, a urological disorder, a kidney disorder, and a congenital defect.

30. The method of claim 1, wherein at least one of the plurality of variables that affect outcome for the data set is a risk factor for a health risk.

31. The method of claim 30, further comprising:
identifying at least one patient having the risk factor.

32. The method of claim 31, further comprising:
providing a preventative treatment for each of the at last one patient having the risk factor.

33. The method of claim 32, wherein the risk factor varies, and wherein the preventative treatment for each of the at least one patient having the risk factor varies depending on variance of the risk factor.

34. A method for delving an outcome predictor for a data set wherein a plurality of variables affect outcome for the data set, the method comprising:
randomly selecting a holdout sample from the data set;
withdrawing the holdout sample from the data set, such that a remainder data set and a holdout data set are created;
generating basis functions for interactions among the plurality of variables for the data set using Multivariate Adaptive Regression Splines;
determining rules far the generated basis functions relating to the interactions among the plurality of variables;
applying a Classification and Regression Trees recursive partitioning methodology to the data set, using the rules determined for the generated basis functions, to produce the outcome predictor;
verifying the outcome predictor;
wherein the outcome predictor is verified using 10-fold cross validation; and
outputting the outcome predictor.

35. The method of claim 34, wherein verifying the outcome predictor includes:
applying the recursive partitioning methodology to a holdout data set.

36. A method for deriving an outcome predictor for a data set, wherein a plurality of variables affect outcome for the data set, the method comprising:
randomly selecting a holdout sample from the data set;
withdrawing the holdout sample from the data set, such that a remainder data set and a holdout data set are created;

generating basis functions for interactions among the plurality of variables for the data set using Multivariate Adaptive Regression Splines;

determining rules for the generated basis functions relating to the interactions among the plurality of variables;

applying a Classification and Regression Trees recursive partitioning methodology to the data set, using the rules determined for the generated basis functions, to produce the outcome predictor; and outputting the outcome predictor;

wherein the plurality of variables include at least one target drug;

wherein the data set includes genotypic data; and wherein the outcome predictor is used to determine a personalized treatment regimen for an individual.

37. A method for deriving an outcome predictor for a data set, wherein a plurality of variables affect outcome for the data set, the method comprising:

randomly selecting a holdout sample from the data set;

withdrawing the holdout sample from the data set, such that a remainder data set and a holdout data set are created;

generating basis functions for interactions among the plurality of variables for the data set using Multivariate Adaptive Regression Splines;

determining rules for the generated basis functions relating to the interactions among the plurality of variables;

applying a Classification and Regression Trees recursive partitioning methodology to the data set, using the rules determined for the generated basis functions, to produce the outcome predictor; and outputting the outcome predictor;

wherein applying a recursive partitioning methodology to the data set using the generated basis functions to produce the outcome predictor includes selecting a target drug.

38. A method for deriving an outcome predictor for a data set, wherein a plurality of variables affect outcome for the data set, the method comprising:

randomly selecting a holdout sample from the data set;

withdrawing the holdout sample from the data sets such that a remainder data set and a holdout data set are created;

generating basis functions for interactions among the plurality of variables for the data set using Multivariate Adaptive Regression Splines;

determining rules for the generated basis functions relating to the interactions among the plurality of variables;

applying a Classification and Regression Trees recursive partitioning methodology to the data set, using the rules determined for the generated basis functions, to produce the outcome predictor; and outputting the outcome predictor;

wherein an individual has a genotype, wherein the outcome predictor comprises a decision tree containing a result for the phenotype of the individual, and wherein the individual has a disease.

* * * * *